(12) United States Patent
Buffa et al.

(10) Patent No.: US 6,551,997 B1
(45) Date of Patent: Apr. 22, 2003

(54) ENGINEERED POLYPEPTIDES IN PERSONAL CARE APPLICATIONS

(75) Inventors: Charles W. Buffa, Teaneck, NJ (US); Anthony J. O'Lenick, Jr., Dacula, GA (US); Megan Genzale, N. Arlington, NJ (US)

(73) Assignee: Biosil Research Institute INC, Paterson, NJ (US)

( * ) Notice: Subject to any disclaimer, the term of this patent is extended or adjusted under 35 U.S.C. 154(b) by 0 days.

(21) Appl. No.: 10/127,039

(22) Filed: Apr. 22, 2002

(51) Int. Cl.[7] .................. A61K 38/00; A61K 39/395; C12P 21/06

(52) U.S. Cl. .............. 514/12; 424/177; 514/2; 514/21; 514/880; 530/407; 435/68.1

(58) Field of Search .............. 424/177; 514/2, 514/12, 21, 880; 435/68.1; 530/407

(56) References Cited

U.S. PATENT DOCUMENTS 5,314,873 A    5/1994  Tamita et al.

*Primary Examiner*—Brenda Brumback
*Assistant Examiner*—B. Dell Chism

(57) ABSTRACT

The present invention is directed to process for conditioning hair and skin in which the skin has applied to it a polypeptide having between 20 and 60 amino acids in a polypeptide, having cysteine as at least 10% of the amino acids units and proline as at least 5% of the amino acid units.

2 Claims, No Drawings

ENGINEERED POLYPEPTIDES IN PERSONAL CARE APPLICATIONS

FIELD OF THE INVENTION

The present invention relates to synthetic polypeptides that are made by the reaction of amino acids to give specific compounds that have outstanding properties when applied to hair. The compounds of the present invention are rich relatively low molecular weight polypeptides, having a molecular weight up to 2000 Daltons. These polypeptides are rich in sulfur bearing amino acids, most specifically cysteine and are also rich in proline. This low molecular weight and the enhanced content of specific amino acids results in (a) essentially linear proteins; (b) penetration of the hair shaft due to lower molecular weight and (c) reaction with treated hair to reform di-sulfide bonds between the natural sulfur bearing amino acids in the hair protein and the polypeptide.

1. Background

Human hair is treated in a number of ways that affect its structure. The relaxing of hair, bleaching of hair, and permanent waving of the hair are three examples of how chemicals are applied to the hair in an attempt to alter its structure. The processes all open up the disulfide bond that is present in hair. It is this disulfide bond that regulates the curl in the hair and many other properties. Since the treatment of hair is very harsh to the hair, it is highly desirable to apply materials to treat the hair to minimize ongoing damage and to preserve the intended effect. Proteins per se are not generally effective in conditioning hair, since they are too large in molecular weight to penetrate the hair. Polypeptides can be effective if they are low enough molecular weight to penetrate. Many companies call these polypeptides made by hydrolysis "proteins".

Heretofore, these "proteins" applied to the hair for conditioning and antistatic effect have been made by hydrolysis of natural proteins. The hydrolysis procedure makes use of either acidic alkaline or enzymatic processes. These processes actually destroy peptide bonds giving a mixture of different molecular weight polypeptides, and amino acids. This approach results in materials that have low efficiency on the hair.

The reason for this low efficiency is the fact that in hydrolysis the entire protein is reacted giving many polypeptides that have little or no functionality on hair. This lack of functionality may be due to (a) the fact that the polypeptide segments are globular, rather than linear, (b) the polypeptide contains little or no sulfur rich amino acids and (c) the polypeptide fails to penetrate the hair because they are too high molecular weight to penetrate the hair. We have surprisingly found that by synthesizing the amino acid sequence of interest, rather than degrading natural proteins, a highly functional product can be achieved. The polypeptide we synthesize is referred to as engineered polypeptides and can either be made in the laboratory using a protein synthesizer or can be made using genetically modified microbes like bacteria. Interestingly, these proteins will therefore not be based upon animal protein, making them of interest to today's personal care market, where animal rights are a grave concern to many Typical of the hydrolyzed protein U.S. Pat. No. 5,314,873 issued on May 24, 1994 to Tomita et al. It discloses the treatment of milk protein by hydrolysis to make hair and skin treating agents. This patent and others like it make use of native proteins that are degraded into polypeptides. The elevate levels of sulfur rich amino acids and proline are absent from these compounds.

3. The Invention

OBJECT OF THE INVENTION

Therefore, it is an object of the present invention to provide specific polypeptides having a molecular weight of up to 2,000 Daltons that are rich in sulfur bearing amino acids like cysteine and are likewise rich in the amino acid proline.

It is also an objective of the present invention to provide a process for treating hair that comprises contacting the hair with an effective conditioning amount of a specific polypeptide having a molecular-weight of up to 2,000 Daltons that are rich in sulfur bearing amino acids like cysteine and are likewise rich in the amino acid proline.

SUMMARY OF THE INVENTION

The present invention is related to a sequence of amino acids having between 20 and 60 amino acids in a polypeptide. In the sequence having 20 amino acid units, at least 2 cysteine units and at least 1 proline unit are present. In a sequence having 60 amino acids in the polypeptide, at least 6 cysteine units and at least 3 proline units are present.

DETAILED DESCRIPTION OF THE INVENTION

The present invention allows for the custom synthesis of polypeptides that have specific functionality in conditioning hair. The presences of specific groups in the polypeptide at specific concentrations. Specifically, cysteine a sulfur rich amino acid must be present at a concentration that allows for it to react with native cysteine in the hair to keep the shape of the hair as treated. Cysteine is found in low concentrations in normal hair and the formation of the disulfide bond is generally attributed to the curl in hair. Additionally, proline, referred to as the coil breaker amino acid must be present at a suitable concentration in the molecule. This causes the polypeptide to be essentially linear rather than globular and allows for the cysteine's sulfur group to bind with the hair's sulfur groups.

Finally, the molecular weight needs to be low enough to penetrate the hair. Therefore, the polypeptide of the present invention will have between 20 and 60 amino acids in its sequence. It will have between 10% and 33% of those units being cysteine and between 5% and 15% proline. The remaining amino acid units in the polypeptide will be made up of some or all other amino acids.

The present invention provides for a process for conditioning hair and skin which comprises contacting the hair or skin with an effective conditioning concentration of a polypeptide having between 20 and 60 amino acids in a polypeptide, having cysteine as at least 10% of the amino acids units and proline as at least 5% of the amino acid units. The effective conditioning concentration ranges from between 0.1% and 25% by weight.

PREFERRED EMBODIMENTS

In a preferred embodiment the polypeptide has 20 amino acid units linked together, in which at least 2 units are cysteine and 1 is proline.

In a preferred embodiment the polypeptide has 20 amino acid units linked together, in which at least 2 units are cysteine and 1 is proline, with the proline unit being in the center of the molecule.

In a preferred embodiment the polypeptide has 40 amino acid units linked together, in which at least 2 units are cysteine, distributed throughout the molecule, and 1 is proline, with the proline unit being in the center of the molecule.

In a preferred embodiment the polypeptide has 60 amino acid units linked together, in which at least 6 units are cysteine and 3 is proline.

In a preferred embodiment the polypeptide has 40 amino acid units linked together, in which at least 6 units are cysteine and 3 is proline, with the proline units being distributed throughout the molecule.

In a preferred embodiment the polypeptide has 40 amino acid units linked together, in which at least 4 units are cysteine and 2 is proline.

In a preferred embodiment the polypeptide has 20 amino acid units linked together, in which at least 4 units are cysteine and 2 is proline, with the proline units being distributed throughout the molecule.

EXAMPLES

Short polypeptide sequences can be made at a variety of locations including the HHMI Biopolymer/Keck Foundation Biotechnology Resource Laboratory at Yale University Synthetic peptides were made up to 40 residues. All peptides that can be purified are chromatographed on a preparative C-18 or C-4 RP-HPLC system and delivered as a lyophilized material. Yields for normal peptides under 40 residues are "guaranteed" at 50 mg or more and at 90+% purity.

Products of This Invention

| Example | Amino Acid Total |
|---|---|
| 1 | 20 |

Amino Acid Sequence: (SEQ ID NO. Example 1)
Ala-Leu-Arg-Ser-Cys-Leu-Pro-Ala-Lys-Ser-Ala-Leu-Arg-Ser-Cys-Leu-Pro-Ala-Lys-Ser

| Example | Amino Acid Total |
|---|---|
| 3 | 20 |

Amino Acid Sequence: (SEQ ID NO. Example 2)
Ala-Leu-Arg-Ser-Cys-Leu-Ala-Lys-Pro-Ser-Ala-Leu-Arg-Ser-Cys-Leu-Pro-Ala-Lys-Ser

| Example | Amino Acid Total |
|---|---|
| 3 | 40 |

Amino Acid Sequence: (SEQ ID NO. Example 3)
Ala-Leu-Arg-Ser-Cys-Leu-Ala-Lys-Pro-Ser-Ala-Leu-Arg-Ser-Cys-Leu-Pro-Ala-Lys-Ser-
Ala-Leu-Arg-Ser-Cys-Leu-Ala-Lys-Pro-Ser-Ala-Leu-Arg-Ser-Cys-Leu-Pro-Ala-Lys-Ser

| Example | Amino Acid Total |
|---|---|
| 4 | 60 |

Amino Acid Sequence (SEQ ID NO. Example 4)
Ala-Leu-Arg-Ser-Cys-Leu-Ala-Lys-Pro-Ser-Ala-Leu-Arg-Ser-Cys-Leu-Pro-Ala-Lys-Ser-
Ala-Leu-Arg-Ser-Cys-Leu-Ala-Lys-Pro-Ser-Ala-Leu-Arg-Ser-Cys-Leu-Lys-Ala-Lys-
Ser-Ala-Leu-Arg-Ser-Cys-Leu-Ala-Lys-Pro-Ser-Ala-Leu-Arg-Ser-Cys-Leu-Lys-Ala-
Lys-Ser

| Example | Amino Acid Total |
|---|---|
| 5 | 40 |

Amino Acid Sequence: (SEQ ID NO. Example 5)
Ala-Leu-Arg-Ser-Cys-Leu-Ala-Lys-Pro-Ser-Ala-Leu-Arg-Ser-Cys-Leu-Pro-Ala-Lys-
Cys-Ala-Leu-Arg-Ser-Cys-Leu-Ala-Lys-Cys-Pro-Ser-Ala-Leu-Arg-Ser-Cys-Leu-Pro-
Ala-Lys

| Example | Amino Acid Total |
|---|---|
| 6 | 40 |

Amino Acid Sequence: (SEQ ID NO. Example 6)
Ala-Leu-Arg-Ser-Cys-Leu-Ala-Lys-Pro-Ser-Ala-Leu-Arg-Ser-Cys-Leu-Ala-Lys-Cys-
Ala-Leu-Arg-Ser-Cys-Leu-Ala-Lys-Cys-Pro-Ser-Ala-Leu-Arg-Ser-Ser-Arg-Leu-Pro-
Ala-Lys

| Example | Amino Acid Total |
|---|---|
| 7 | 20 |

Amino Acid Sequence: (SEQ ID NO. Example 7)
Ala-Leu-Arg-Ser-Cys-Leu-Ala-Lys-Pro-Ser-Ala-Leu-Arg-Ser-Cys-Leu-Ser-Ala-Lys-Ser-
Ala-Leu-Arg-Ser-Cys-Leu-Ala-Lys-Pro-Ser-Ala-Leu-Arg-Ser-Cys-Leu-Ser-Ala-Lys-Ser -continued Products of This Invention

| Example | Amino Acid Total |
|---|---|
| 9 | 20 |

Amino Acid Sequence: (SEQ ID NO. Example 8)
Ala-Pro-Arg-Ser-Cys-Leu-Ala-Lys-Pro-Ser-Ala-Leu-Arg-Ser-Cys-Leu-Ser-Ala-Cys-Ser Comparative Examples

| Example | Amino Acid Total |
|---|---|
| 9 | 20 |

Amino Acid Sequence: (SEQ ID NO. Example 9)
Ala-Leu-Arg-Ser-Ser-Leu-Ala-Lys-Lys-Ser-Ala-Leu-Arg-Ser-Lys-Leu-Ala-Ala-Lys-Ser

| Example | Amino Acid Total |
|---|---|
| 10 | 40 |

Amino Acid Sequence: (SEQ ID NO. Example 10)
Ala-Leu-Arg-Ser-Ser-Leu-Ala-Cys-Lys-Ser-Ala-Leu-Arg-Ser-Lys-Leu-Ala-Ala-Lys-Ser-
Ala-Leu-Arg-Ser-Ser-Leu-Ala-Lys-Ala-Ser-Ala-Leu-Arg-Ser-Ser-Leu-Ala-Ala-Lys-Pro

| Example | Amino Acid Total |
|---|---|
| 11 | 20 |

Amino Acid Sequence: (SEQ ID NO. Example 11)
Ala-Leu-Arg-Ser-Ser-Leu-Ala-Lys-Lys-Ser-Ala-Leu-Arg-Ser-Lys-Leu-Ala-Ala-Lys-Ser-
Ala-Leu-Arg-Ser-Ser-Leu-Ala-Cys-Ala-Ser-Ala-Leu-Arg-Ser-Ser-Leu-Ala-Ala-Lys

APPLICATIONS EXAMPLES

Test Method:

The test hair used was 7-inch dark brown virgin hair from DeMeo Brothers. Five two-gram tresses were used per product evaluated. All tresses were pre-washed three times with PRELL$^R$ original shampoo, rinsed in water at 25° C., and air-dried.

Test Scale

1 Very poor
2 Poor
3 Satisfactory
4 Good
5 Excellent

Formulations Tested

1. Base Formulation
2. 1.0% polypeptide 1 added to Base Formula
3. 1.0% polypeptide 2 added to Base Formula
4. 1.0% polypeptide 3 added to Base Formula
5. 1.0% polypeptide 4 added to Base Formula
6. 1.0% polypeptide 5 added to Base Formula
7. 1.0% polypeptide 6 added to Base Formula
8. 1.0% polypeptide 7 added to Base Formula
9. 1.0% polypeptide 8 added to Base Formula
10. 1.0% polypeptide 9 added to Base Formula
11. 1.0% polypeptide 10 added to Base Formula
12. 1.0% polypeptide 11 added to Base Formula

| Base Formulation | | |
|---|---|---|
| A) | Water | Qs 100.00 |
| | Methyl Paraben | 0.15 |
| | Tetrasodium EDTA | 0.05 |
| B) | Rice Bran Oil | 4.00 |
| | Cetyl Alcohol | 3.00 |
| | Test Ingredient* | 1.00 |
| | Glyceryl Stearate | 2.50 |
| | Propylparben | 0.10 |
| C) | Germall 115 | 0.20 |

*1% by weight of the 100% active polypeptide is added.

Procedure

1. In a suitable container, weigh out all items in phase A in order shown.
2. Mix well heating to 75 C.
3. In a separate container weigh out and combine all items in Phase B in the order shown.
4. Heat Phase B to 75 C.
5. Add Phase B to Phase A at 75 C, agitating for at least 15 minutes.
6. Add Phase C.
7. Cool to 25–30C.

Comb Properties

The evaluations were made using both visual and tactile observations.

Evaluation

Formulation 1 (Base Formula)

| | |
|---|---|
| Residual Feel | 2 |
| Squeaky Feel | 1 |
| Shine | 1 |
| Wet Combing | 2 |
| Product Spreadbility | 2 |
| Smoothness of Product | 2 |

Formulation 2 (1.0% polypeptide 1 added to Base Formula)

| | |
|---|---|
| Residual Feel | 4 |
| Squeaky Feel | 3 |
| Shine | 3 |
| Wet Combing | 5 |
| Product Spreadbility | 5 |
| Smoothness of Product | 5 |

Formulation 3 (1.0% polypeptide 2 added to Base Formula)

| | |
|---|---|
| Residual Feel | 4 |
| Squeaky Feel | 2 |
| Shine | 2 |
| Wet Combing | 5 |
| Product Spreadbility | 4 |
| Smoothness of Product | 4 |

Formulation 4 (1.0% polypeptide 3 added to Base Formula)

| | |
|---|---|
| Residual Feel | 4 |
| Squeaky Feel | 3 |
| Shine | 3 |
| Wet Combing | 4 |
| Product Spreadbility | 4 |
| Smoothness of Product | 4 |

Formulation 5 (1.0% polypeptide 4 added to Base Formula)

| | |
|---|---|
| Residual Feel | 3 |
| Squeaky Feel | 4 |
| Shine | 3 |
| Wet Combing | 4 |
| Product Spreadbility | 4 |
| Smoothness of Product | 4 |

Formulation 6 (1.0% polypeptide 5 added to Base Formula)

| | |
|---|---|
| Residual Feel | 4 |
| Squeaky Feel | 3 |
| Shine | 4 |
| Wet combing | 5 |
| Product Spreadbility | 4 |
| Smoothness of Product | 4 |

Formulation 7 (1.0% polypeptide 6 added to Base Formula)

| | |
|---|---|
| Residual Feel | 4 |
| Squeaky Feel | 3 |
| Shine | 3 |
| Wet Combing | 4 |
| Product Spreadbility | 4 |
| Smoothness of Product | 4 |

Formulation 8 (1.0% polypeptide 7 added to Base Formula)

| | |
|---|---|
| Residual Feel | 3 |
| Squeaky Feel | 3 |
| Shine | 3 |
| Wet Combing | 4 |
| Product Spreadbility | 4 |
| Smoothness of Product | 3 |

Formulation 9 (1.0% polypeptide 8 added to Base Formula)

| | |
|---|---|
| Residual Feel | 4 |
| Squeaky Feel | 3 |
| Shine | 2 |
| Wet Combing | 5 |
| Product Spreadbility | 4 |
| Smoothness of Product | 4 |

Comparative Data

Formulation 10 (1.0% polypeptide 9 added to Base Formula)

| | |
|---|---|
| Residual Feel | 2 |
| Squeaky Feel | 1 |
| Shine | 1 |
| Wet Combing | 2 |
| Product Spreadbility | 2 |
| Smoothness of Product | 3 |

Formulation 11 (1.0% polypeptide 10 added to Base Formula)

| | |
|---|---|
| Residual Feel | 2 |
| Squeaky Feel | 2 |
| Shine | 2 |
| Wet Combing | 3 |
| Product Spreadbility | 2 |
| Smoothness of Product | 3 |

As can be easily seen from the above data, the compounds of the present invention condition hair and provide additional benefits to the hair.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A process for conditioning hair which comprises contacting the hair with an effective conditioning concentration of a polypeptide having between 20 and 60 amino acids in a polypeptide, having between 10% and 15% of the amino acids units cysteine and between 6.6 and 10% of the amino acid units proline.

2. A process of claim 1 wherein the effective conditioning concentration ranges from 0.1% to 25% by weight.

* * * * *

SEQUENCE LISTING

<160> NUMBER OF SEQ ID NOS: 11

<210> SEQ ID NO 1
<211> LENGTH: 20
<212> TYPE: PRT
<213> ORGANISM: Escherichia coli

<400> SEQUENCE: 1

Ala Leu Arg Ser Cys Leu Pro Ala Lys Ser Ala Leu Arg Ser Cys Leu
1               5                   10                  15

Pro Ala Lys Ser
            20

<210> SEQ ID NO 2
<211> LENGTH: 20
<212> TYPE: PRT
<213> ORGANISM: Escherichia coli

<400> SEQUENCE: 2

Ala Leu Arg Ser Cys Leu Ala Lys Pro Ser Ala Leu Arg Ser Cys Leu
1               5                   10                  15

Pro Ala Lys Ser
            20

<210> SEQ ID NO 3
<211> LENGTH: 40
<212> TYPE: PRT
<213> ORGANISM: Escherichia coli

<400> SEQUENCE: 3

Ala Leu Arg Ser Cys Leu Ala Lys Pro Ser Ala Leu Arg Ser Cys Leu
1               5                   10                  15

Pro Ala Lys Ser Ala Leu Arg Ser Cys Leu Ala Lys Pro Ser Ala Leu
            20                  25                  30

Arg Ser Cys Leu Pro Ala Lys Ser
        35                  40

<210> SEQ ID NO 4
<211> LENGTH: 60
<212> TYPE: PRT
<213> ORGANISM: Escherichia coli

<400> SEQUENCE: 4

Ala Leu Arg Ser Cys Leu Ala Lys Pro Ser Ala Leu Arg Ser Cys Leu
1               5                   10                  15

Pro Ala Lys Ser Ala Leu Arg Ser Cys Leu Ala Lys Pro Ser Ala Leu
            20                  25                  30

Arg Ser Cys Leu Lys Ala Lys Ser Ala Leu Arg Ser Cys Leu Ala Lys
        35                  40                  45

Pro Ser Ala Leu Arg Ser Cys Leu Lys Ala Lys Ser
    50                  55                  60

<210> SEQ ID NO 5
<211> LENGTH: 40
<212> TYPE: PRT
<213> ORGANISM: Escherichia coli

<400> SEQUENCE: 5

Ala Leu Arg Ser Cys Leu Ala Lys Pro Ser Ala Leu Arg Ser Cys Leu
1               5                   10                  15

-continued

Pro Ala Lys Cys Ala Leu Arg Ser Cys Leu Ala Lys Cys Pro Ser Ala
                20                  25                  30

Leu Arg Ser Cys Leu Pro Ala Lys
        35                  40

<210> SEQ ID NO 6
<211> LENGTH: 40
<212> TYPE: PRT
<213> ORGANISM: Escherichia coli

<400> SEQUENCE: 6

Ala Leu Arg Ser Cys Leu Ala Lys Pro Ser Ala Leu Arg Ser Cys Leu
1               5                   10                  15

Ala Lys Cys Ala Leu Arg Ser Cys Leu Ala Lys Cys Pro Ser Ala Leu
                20                  25                  30

Arg Ser Ser Arg Leu Pro Ala Lys
        35                  40

<210> SEQ ID NO 7
<211> LENGTH: 40
<212> TYPE: PRT
<213> ORGANISM: Escherichia coli

<400> SEQUENCE: 7

Ala Leu Arg Ser Cys Leu Ala Lys Pro Ser Ala Leu Arg Ser Cys Leu
1               5                   10                  15

Ser Ala Lys Ser Ala Leu Arg Ser Cys Leu Ala Lys Pro Ser Ala Leu
                20                  25                  30

Arg Ser Cys Leu Ser Ala Lys Ser
        35                  40

<210> SEQ ID NO 8
<211> LENGTH: 20
<212> TYPE: PRT
<213> ORGANISM: Escherichia coli

<400> SEQUENCE: 8

Ala Pro Arg Ser Cys Leu Ala Lys Pro Ser Ala Leu Arg Ser Cys Leu
1               5                   10                  15

Ser Ala Cys Ser
                20

<210> SEQ ID NO 9
<211> LENGTH: 20
<212> TYPE: PRT
<213> ORGANISM: Escherichia coli

<400> SEQUENCE: 9

Ala Leu Arg Ser Ser Leu Ala Lys Ser Ala Leu Arg Ser Lys Leu
1               5                   10                  15

Ala Ala Lys Ser
                20

<210> SEQ ID NO 10
<211> LENGTH: 40
<212> TYPE: PRT
<213> ORGANISM: Escherichia coli

<400> SEQUENCE: 10

Ala Leu Arg Ser Ser Leu Ala Cys Lys Ser Ala Leu Arg Ser Lys Leu
1               5                   10                  15

```
Ala Ala Lys Ser Ala Leu Arg Ser Ser Leu Ala Lys Ala Ser Ala Leu
            20                  25                  30

Arg Ser Ser Leu Ala Ala Lys Pro
            35                  40

<210> SEQ ID NO 11
<211> LENGTH: 39
<212> TYPE: PRT
<213> ORGANISM: Escherichia coli

<400> SEQUENCE: 11

Ala Leu Arg Ser Ser Leu Ala Lys Lys Ser Ala Leu Arg Ser Lys Leu
1               5                   10                  15

Ala Ala Lys Ser Ala Leu Arg Ser Ser Leu Ala Cys Ala Ser Ala Leu
            20                  25                  30

Arg Ser Ser Leu Ala Ala Lys
            35
```